United States Patent [19]

Lin et al.

[11] 4,092,219

[45] May 30, 1978

[54] PREPARATION OF ENZYME-MEMBRANE COMPLEXES

[76] Inventors: Po-Min Lin, 714 Bevier Rd., Piscataway, N.J. 08854; Jack R. Giacin, 2 Stanworth La., Allentown, N.J. 08501; Seymour G. Gilbert, 74 N. Ross Hall Blvd., Piscataway, N.J. 08854; Joseph G. Leeder, 379 Huff Rd., North Brunswick, N.J. 08902

[21] Appl. No.: 604,131

[22] Filed: Aug. 13, 1975

[51] Int. Cl.² .......................... C07G 7/00; C07G 7/02
[52] U.S. Cl. ........................................ 195/29; 195/5; 195/63; 195/68; 195/DIG. 11
[58] Field of Search .................. 195/63, 68, DIG. 11, 195/4, 5, 29; 204/181; 106/161

[56] References Cited

U.S. PATENT DOCUMENTS

| | | | |
|---|---|---|---|
| 2,920,000 | 1/1960 | Hochstadt et al. | 106/161 |
| 3,758,396 | 9/1973 | Vieth et al. | 204/181 |
| 3,843,446 | 10/1974 | Vieth et al. | 195/68 |

OTHER PUBLICATIONS

Lin, et al., Chemical and Enzymatic Modification of Collagen-Effect on the Enzyme Binding Capacity, Abstract Present at the Annual Meeting of the Institute of Food Technologists, New Orleans, Louisiana, May 12-15, 1974.

Venkatzsubramanian, et al., Immobilization of Papain on Collagen and the Use of Collagen-Papain Membranes in Beef Chill-Proofing, Journal of Food Science, vol. 40, No. 1, Jan. 1975, (pp. 109–113).

Olson, et al., Immobilized Enzymes in Food and Microbial Processes, Plenum Press, N.Y., 1974, (pp. 157–171).

*Primary Examiner*—David M. Naff
*Attorney, Agent, or Firm*—Lerner, David, Littenberg & Samuel

[57] ABSTRACT

The amount of enzyme complexed to a protein membrane is increased by treating the protein before or after forming the membrane with a proteolytic enzyme. Preferred proteolytic enzymes are pepsin, trypsin and pronase. Treatment is carried out at a temperature between 15° and 25° C for a period of 1 to 12 hours. Enzymes are complexed to the protein membrane, after treatment, by swelling and washing the membrane and contacting the membrane with an enzyme.

14 Claims, 2 Drawing Figures

PREPARATION OF ENZYME-MEMBRANE COMPLEXES

FIELD OF THE INVENTION

The present invention relates to improved protein-enzyme complexes in membrane form. More specifically, the present invention relates to such improved enzyme-membrane complexes useful in catalyzing enzymatic reactions. Still more specifically, the present invention relates to methods for preparing protein membranes for use in protein-enzyme complexes. Still more specifically, the present invention relates to a method for preparing enzyme-membrane complexes and for using such complexes as enzymatically active membranes.

DESCRIPTION OF THE PRIOR ART

Enzymes are biological catalysts that regulate a multitude of chemical reactions occurring in the living cell. Such enzymes, or protein catalysts, have therefore been used for a wide variety of industrial and research applications, particularly in the areas of foods, pharmaceuticals, paper, textile processing, etc. Enzyme reactions are industrially advantageous for several reasons, including their high degree of substrate specificity, their ability to eliminate the production of undesirable by-products, high reaction velocities, reduced manufacturing costs, and the elimination of severe processing conditions, reducing the possibility of damage to heat sensitive substrates.

While in the past soluble enzyme systems have been employed for such purposes, more recently the use of immobilized enzymes has become increasingly important. The reasons for these are several, including the ability to reuse the enzymes employed, the potential for continuous processing, improved stability of the enzymes so-employed, etc. Such immobilized enzymes are those in which the enzymes are immobilized or bound to inert or insoluble carriers. Thus, at the completion of the enzymatic reactions, these insoluble enzyme-containing materials can be separated from the unreacted substrate or product by techniques such as ultrafiltration or the like.

The selection of a suitable inert carrier, however, has been quite difficult, since the carrier must not only be inert to the enzyme, but it must not inhibit the catalytic activity of the enzyme, nor cause undesirable unspecific adsorption. Moreover, the carrier should present a minimum of steric hindrance toward the enzyme-substrate reaction. A wide variety of prior art carriers have been proposed, depending upon the particular type of enzyme used and the particular enzymatic reaction desired. For instance, among those prior art carriers disclosed in the open literature are included synthetic polymers such as polyamides, cellulose derivatives, various clays, and ion-exchange resins, particularly DEAE-cellulose, and DEAE-dextrans, as discussed in Suzuki, et al., Agr. Biol. Chem., and the methods of preparing immobolized enzymes have included direct covalent bonding, indirect covalent bonding through an intermediate compound, crosslinking of the enzyme or trapping the enzyme in polymer lattices.

None of these prior art techniques or carriers, however, have been entirely satisfactory for all purposes. Synthetic polymer carriers are expensive and frequently are not readily available. Moreover, they often require special treatment in order to chemically bind the enzyme to the carrier. Ion-exchange resins, such as DEAE-cellulose and DEAE-dextran, have ion-exchange properties, which may not be desirable for certain applications. The problem of enzyme liberation from a carrier is one weak point in many immobilized enzyme preparations, and is particularly troublesome in the case of amylase bound to acid clay, which becomes liberated during the hydrolytic reaction of starch.

Recently, however, a new enzyme carrier was disclosed in U.S. Pat. No. 3,843,446 to Vieth et al. This carrier thus principally comprises a protein membrane, disclosed as including either a synthetic polypeptide or a natural protein in both modified or unmodified forms. This patent thus describes enzyme immobilization on such carriers by swelling a protein membrane, soaking the membrane in an aqueous dispersion of an enzyme in order to complex the enzyme with the protein, and drying.

While such protein-membrane complexes have proven quite successful, it has been desirable to incorporate greater amounts of enzymes into the protein membrane in order to provide more desirable commercial enzymatic reactors.

SUMMARY OF THE INVENTION

According to the present invention it has now been discovered that the enzyme binding capacity of certain types of protein membranes can be significantly increased by treatment with a specific type of proteolytic enzyme prior to contacting the protein membrane with a compatible enzyme solution.

Specifically, there are several methods for preparing a protein membrane. Generally these involve the initial preparation of a suspension of the protein fibrils, and the subsequent extrusion or casting of this suspension into a suitable membrane form. In the past, the thus-prepared protein membranes have been swollen, generally washed until a desired pH level is obtained for the particular enzyme being complexed, and then soaked in an aqueous enzyme-containing solution so that the enzyme complexes with the protein membrane. According to the present invention, certain types of valuable proteins, either in the dispersed form or in the film form, are treated with a particular type of proteolytic enzyme, such as pepsin, prior to impregnation with the desired enzyme.

Such protein membranes have also been modified, primarily by either chemical or natural means, in order to promote the formation of cross-linkages and principally to enhance the film or membrane's tensile strength. The chemical formation of such cross-linkages has generally involved the use of formaldehyde, glutaraldehyde, chromic acid, etc. On the other hand, improved mechanical strength can also be attained in the protein film by natural cross-linking, i.e., by allowing the film to age, or by rapid aging, i.e., by annealing. It has been found, however, that in each of these cases, as the tensile or mechanical strength of the protein films or membranes increases, there has been a concommitant decrease in the enzyme binding capacity of these membranes. It is thus theorized that the matrix structure of the protein film has been modified so that the binding of enzymes is adversely affected. It thus appears that the number of potential sites for enzyme bonding is reduced as the mechanical properties are increased by further cross-linking of the protein membrane. According to the present invention it has now been discovered that the mechanical strength of such protein membranes, particularly those which have been tanned with chemical reagents such as glutaraldehyde or which have been aged, can be maintained, while at the same time the enzyme binding capacity of such films can be greatly increased, by the present treatment with certain proteolytic enzymes, such as pepsin. In this manner, protein-enzyme membranes including greater than about 50 mgs of enzyme per gram of protein-enzyme complex, preferably greater than about 100 mgs of enzyme per gram of protein-enzyme complex, can now be prepared. In particular when $\beta$-galactosidase is employed, for example, greater than 100 mgs of enzyme per gram of protein-enzyme complex, and preferably greater than 150 mgs of enzyme per gram of protein-enzyme complex can result.

BREIF DESCRIPTION OF THE DRAWINGS

FIG. 1 is a graphic representation demonstrating the effect of pepsin treatment on enzyme loading capacity of aged collagen film; and FIG. 2 is graphic representation demonstrating the effect of pepsin treatment on cross-linkages of aged collagen films.

DETAILED DESCRIPTION

Figure 1:
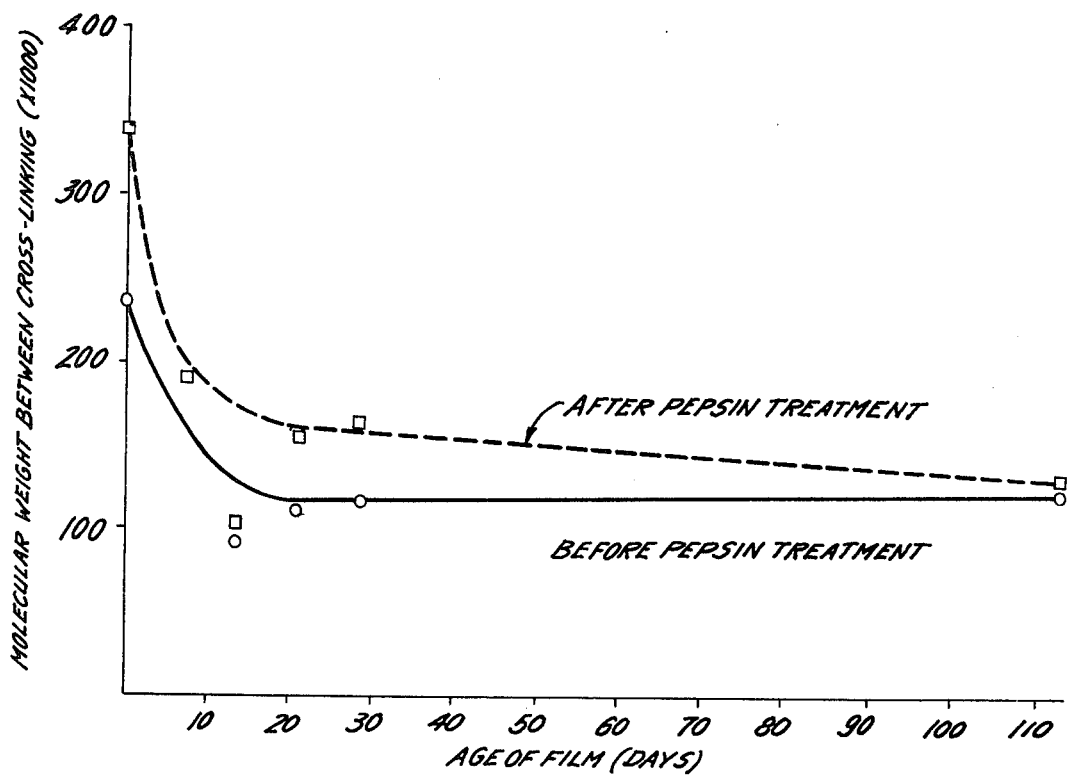

The present invention is specifically directed to certain types of proteins. Specifically, those proteins, be they natural proteins or synthetic polypetides, which include both a well-ordered crystalline region and an amorphous region, may be treated according to the present invention. In particular, the protein collagen has been found to be such a protein which is particularly susceptible to the process of the present invention.

The instant invention thus derives from the treatment of such a protein with a certain type of proteolytic enzyme. Specifically, a proteolytic enzyme which does not attack the well-ordered crystalline or helical region of the protein, but only the amorphous or telopeptide region thereof, is employed. As stated above, in this manner, it has now been discovered that the enzyme binding capacity of the so-treated protein can be significantly increased, both with respect to freshly cast protein membranes and most significantly with respect to protein which includes substantial cross-linking, either by chemical or natural means, such as aging.

In a preferred embodiment, the protein collagen, which is a protein including a well-ordered crystalline region and a non-ordered or amorphous region is employed, and various proteolytic enzymes other than the enzyme collagenase are employed for treating the collagen. That is, collagenase will attack the ordered or crystalline region of collagen. In this embodiment, various other non-collagenase proteases may be employed, including pepsin, trypsin, pronase, etc.

In one embodiment, a collagen film is prepared by casting a dispersion of collagen according to techniques well-known in this art. The film is then swollen, washed in water and soaked in an enzyme solution. After refrigerated storage to allow diffusion of the enzyme into the collagen, the film may be layered on a base, such as a cellulose acetate film, and dried.

Collagen is a glycine-proline rich protein, which is the chief organic constituent of connective animal tissue and bones. Chemically, collagen is distinguishable from other proteins by its unusually high glycine content, which accounts for approximately one-third of the amino acid residues therein; the high content of proline and hydroxyproline; the presence of hydroxyproline, which is unique among proteins; and in having notably small amounts of aromatic and sulfur-containing amino acids. It can be obtained in good yields from a wide variety of mammal and fish parts, and is frequently obtained from pork, sheep and beef tendons; pigskins; tanner's stock, which are calfskins not usable for leather; and ossein, which is tissue obtained by drying cattle bones remaining after acid treatment to remove calcium phosphate.

The collagen molecule includes a well ordered crystalline region which comprises a triple helix, and includes an amorphous or telopeptide region which is non-helical in nature. It is the former region which remains unaffected by the particular proteolytic enzyme employed according to this invention. It has thus been found that the particular proteolytic enzymes employed, such as pepsin, attack the telopeptide-originated cross-linkages in this amorphous region and alters the matrix structure of the film, resulting in the increased diffusion of enzymes into the collagen matrix. In other words, it appears that the cleavage or hydrolysis of the telopeptide-originated linkages permits the enzyme to diffuse more readily throughout the membrane.

The specific mechanism by which this occurs is believed to involve the selective attack of the protease employed upon these telopeptide-originated linkages. In this manner, the cross-linking between corresponding crystalline regions of adjacent protein molecules remain substantially unaffected, thus permitting the protein membrane to retain its physical strength, while at the same time providing a membrane having an improved enzyme binding capacity. A specific demonstration of this effect is contained in the Examples below. In particular, however, it is noted that this proof relates to the method by which cross-linking is established. That is, where the cross-linkages have been naturally produced, such as by aging, or annealing, the total number of cross-links per molecule is relatively low, even with extended aging, and generally ranges from about 3 to 5 cross-links per molecule. These cross-links include linkages between corresponding telopeptide and crystalline (helical) regions of the individual protein molecules, as well as from the telopeptide region of one molecule to the crystalline region of another. Where however, cross-linking is chemically induced, such as by Gluteraldehyde treatment, the total number of cross-linkages is much greater, generally in the range of from about 20 to 50 cross-links per molecule, and again including the three basic types of cross-links described above.

The proteolytic enzyme treatment of the present invention selectively removes these types of cross-links which are telopeptide-involved, i.e., either between corresponding telopeptide regions or from a telopeptide region to a helical region, leaving substantially only cross-linkages between corresponding crystalline or helical regions of adjacent protein molecules. For this reason the positive effect on enzyme loading in the case of naturally aged proteins is much greater, since the total number of helical cross-linkages in the case of chemical cross-linkages remains rather substantial.

Figure 2:
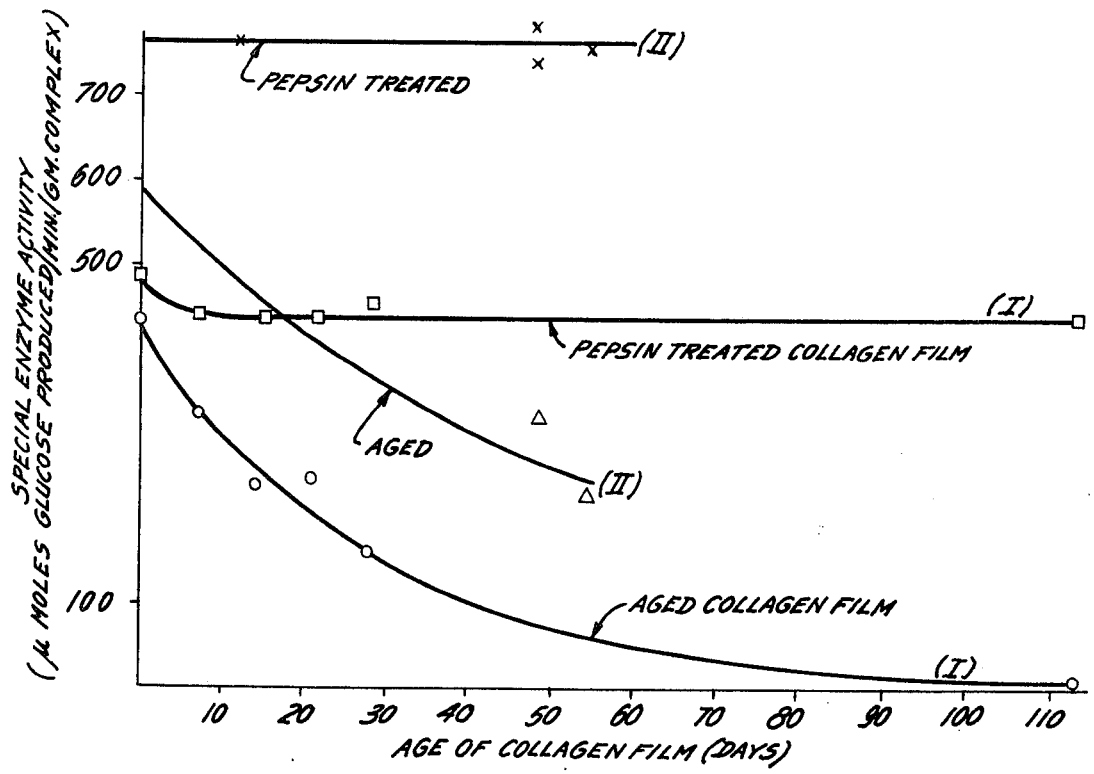

In either case, however, the mechanical strength of the film remains substantially unaffected by the treatment of this invention, i.e., theremaining cross-linkages are sufficient in that regard. This is specifically demonstrated in FIG. 2 hereof, where aged collagen films, with and without pepsin treatment according to this invention, are compared for molecular weight between cross-linkages. The results show that after such pepsin treatment there remain substantial cross-linkages (i.e., mainly in the crystalline region) to maintain the strength of the film. This is, of course, particularly significant from a commercial point of view.

As noted above, the collagen membranes have been formed in several manners in the past. Typically, the collagen source has been intially treated with certain enzymes to dissolve the elastin encircling the collagen fibers. While elastin it itself a protein, the use of these enzymes is directed specifically to this particular protein, and specifically for purposes of assisting in the preparation of the collagen dispersion. While it could be possible to allow for a restricted attack on the telopeptide region of the tropocollagen at this stage, this has not been done in the past, and is not preferred because of operational difficulties. Subsequent to such treatment, the collagen source has then been washed with water, and the soluble proteins or lipids have been removed by treatment with a dilute aqueous solution of a chelating agent, such as ethylene diamine tetrasodium tetraacetate. The collagen fibers have then been swollen in a suitable acid, such as cyanoacetic acid, as described in Hochstadt et al, U.S. Pat. No. 2,920,000, so as to form a collagen fiber dispersion. This dispersion can then be extruded or cast into a suitable membrane form. The dried collagen membrane can then be annealed at about 60° C, 95% R.H. for 48 hours. The collagen fiber dispersion can also be electrodeposited according to British Pat. No. 1,153,551 to form suitable membranes, all of which is incorporated herein by reference thereto.

There are, of course, many additional methods which can be employed to form such collagen, or other protein membranes, and those described herein are merely exemplary of such techniques.

The protein membranes useful in the present invention will generally be from about 0.02 to about 0.08 millimeters thick, preferably from about 0.025 to about 0.05 milliliters thick, and most preferably from about 0.03 to about 0.04 millimeters thick. Thinner membranes tend to be too weak and may include structural defects, i.e., will not be an integral film, while thicknesses are useful where not limited by diffusional resistance.

Other materials may be added to the membrane to accomplish specific aims. For example, plasticizers may be used to modify the molecular structure of the membrane to provide greater resilience by allowing for chain slippage. Humectants like glycerol may maintain a more favorable water binding capacity. Furthermore, cross-linking agents, heating, annealing, or tanning with chromic acid, glutaraldehyde, or formaldehyde, as described above, may also be employed.

The collagen membrane is then prepared for complexing with enzyme, generally by being swollen with a low molecular weight oragnic acid, or in some instances with suitable bases so that the PH ranges from about 2 to about 12. Suitable acids include lactic acid and cyanoacetic acid. Swelling is accomplished by submerging the membrane in the acid bath for between ½ hour and 1 hours, depending upon the particular conditions of the bath, generally at room temperature.

The membrane is swollen by the acidity of the organic acid added and the use of the acid as a plasticizer. No other additive is needed . A change in water binding capacity results rom the acid treatment.

Following the swelling treatment, the swollen collagen membrane is washed thoroughly with water until the pH level of the membrane is within the acceptable range for the particular enzyme being complexed.

As discussed above, either prior to casting of the film, or preferably at this point in the membrane preparation, the protein is treated with the proteolytic enzyme, such as pepsin. Preferably, this step is carried out under very specific conditions. These include a temperature of between about 15° and 25° C, preferably from about 20° to 22° C and for a period of from about 1 to 12 hours, preferably from 2 to 3 hours. Also, the proteolytic enzyme is maintained in an aqueous solution at its respective optimum pH range. For example, when pepsin is used, the pH of the digestion solution is maintained from about 2 to about 4, preferably from about 3 to about 3.5, and preferably for from about 1 to 12 hours; while with pronase the pH of the digestion solution is maintained at from about 6 to 8, preferably at about 7.2 and generally for from about 1 to 6 hours.

Furthermore, as stated above, the prepared film may be aged for a considerable period of time prior to such treatment. Preferably films which have aged from between about 3 to 200 days are particularly susceptible to the present treatment in order to greatly improve their capacity for enzyme complexation.

Finally, the thus-treated protein membrane may then be complexed with the particular enzyme which is desired. For these purposes, the swollen, washed membrane is soaked in an aqueous enzyme-containing solution, until complexing occurs. Usually, this requires a period of from about 12 to 48 hours, preferably from about 24 to 30 hours. The temperature range employed during this time should be maintained from about 4° to 15° C, preferably from about 4° to 10° C, depending upon the particular enzyme employed. Maximum enzyme up-take is measured by activity after washing and indicates when complexing is complete.

The enzyme-protein complex membrane should then be carefully dried, preferably at about room temperature or below, so as not to damage the bound enzyme.

A wide variety of different types of enzymes can be complexed with natural proteins such as collagen and the like in this manner, depending upon the particular application intended. For instance, suitable enzymes include the amylases, oxidoreductases, transferases, hydrolases, and isomerases, such as lysozyme, invertase, urease, cellulases, catecholmethyltransferase, sucrose 6-glucosyl-transferase, carboxyl esterase, aryl esterase, lipase, pectin esterase, glucoamylase, amylopectin-1, 6-glucosidase, oligo-1, 6-glusidase, polygalacturonase, $\alpha$-glucosidase, $\beta$-glucosidase, $\beta$-galactosidase, glucose oxidase, galactose oxidase, catechol oxidase, catalase, peroxidase, lipoxidase, glucose isomerase, pentosanases, cellobiase, xylose isomerase, sulphite oxidase, ethanolamine oxidase, penicillinase, carbonic anhydrase, gluconolactonase, 3-keto steroid $\Delta$ 'dehydrogenase, 11-$\beta$-hydroxylase, and amino acid acylases. Compatible combinations of enxymes, and multienzyme systems, can also be complexed with the collagen in this manner.

Especially suitable, however, are lysozyme, invertase, lactase, urease and amylases. Lysozyme is widely used to hydrolyze microorganisms in pharmaceutical research, and in sewage treatment, either alone or in combination with other enzymes, and/or bacteria. One particularly important application for lysozyme-protein membrane complex is in the lysis of cells.

Invertase of $\beta$-D-fructofuranosidase is widely used in the food and beverage industries, as well as for analytical purposes. Invertase can be used to catalyze the hydrolysis of sucrose to glucose and fructose or invert sugar. Invertase is effective in the hydrolysis of β-D-fructofuranosyl linkages in sucrose, raffinose, gentianose, and methyl and β-fructofructose. One particularly important application for an invertase-protein membrane complex is in the continuous hydrolysis of sucrose.

Urease is a highly specific enzyme which can catalyze the transformation of urea to ammonium carbonate, and is often used to determine the urea content in urine specimens. Because of its highly specific activity, enzyme activity by contacting with the substrate in the following conditions: e.g., an aqueous lactose solution, at a pH of about 7, and temperature of about 37° C for about 10 hours.

Enzyme activity was then measured in terms of micromoles of glucose produced per minutes per gram of complex employed. Also, the actual amount of enzyme bound to the collagen was then determined by measuring the tryptophan content of the complex. The results obtained are contained in Table I hereof. and are also shown in FIG. 1.

TABLE I

EFFECT OF PEPSIN TREATMENT ON ENZYME BINDING CAPACITY OF COLLAGEN FILMS

| Age of Collagen Film (Days) | | | 0 | 7 | 14 | 21 | 28 | 49 | 58 | 113 | 153 |
|---|---|---|---|---|---|---|---|---|---|---|---|
| Apparent Specific Enzyme Activity (μmoles glucose/min/g-complex) | I* | Untreated | 431.26 | 325.38 | 236.08 | 247.33 | 148.62 | — | — | 5.55 | 7.05 |
| | | Pepsin Treated | 490.22 | 438.65 | 431.25 | 431.62 | 457.01 | — | — | 439.94 | 468.40 |
| | II | Untreated | 589.90 | — | — | 406.12 | — | 329.50 | 210.82 | — | — |
| | | Pepsin Treated | 766.77 | — | — | 767.47 | — | 727.50 | 733.60 | — | — |
| Amount of Enzyme* (mg Enzyme/g-complex) | I | Untreated | — | — | — | — | — | — | — | — | 12.5 |
| | | Pepsin Treated | — | — | — | — | — | — | — | — | 51.5 |
| | II | Untreated | — | — | — | — | — | — | 31.5 | — | — |
| | | Pepsin Treated | — | — | — | — | — | — | 207.5 | — | — |

*Average of two determinations one utility for the urease-protein complex membrane is in kidney machine applications. More particularly, urease-protein complex membranes can be used for repeated hydrolysis of urea, such as in the threatment of human wastes.

EXAMPLE 1

Initially, a film approximately 0.05 millimeters thick was prepared from the protein collagen. Specifically, a disperson of collagen in water, at a pH of about 3 was prepared. The dispersion, maintained at approximately room temperature, was prepared by high agitation of the collagen-containing suspension for a period of about 1 to 5 minutes, and at approximately room temperature, following which the solution was de-aerated. The collagen dispersion was then cast into a film by spreading the collagen dispersion upon a flat surface, and allowed to dry for 24 hours at room temperature.

The collagen film was then sliced into a number of small sections, and aged for various lengths of time. Both the unaged film, and the film aged for various perids of time was then divided into two portions, one of which was then contacted with the proteolytic enzyme pepsin. This contacting was carried out in an aqueous solution at approximately 22° C, and for a period of about 3 hours, at a pH of about 3.5. Both the treated and untreated collagen films were then impregnated with enzyme and tested for apparent specific They demonstrate that for freshly cast film while the enzyme activity of a pepsin treated collagen film was greater than that of an untreated film, that after aging the significant maintenance of enzyme activity with the treated film as compared to the untreated film was rather dramatic. Furthermore, the amount of enzyme taken up by the treated collagen film was significantly greater than that taken up by the untreated film, particularly after aging had taken place.

EXAMPLE 2

A similar experiment was conducted upon a collagen dispersion, i.e., prepared in the same manner as the collagen dispersion used in preparing the collagen film of Example 1. In addition, the proteolytic enzyme employed in Example 2 was pronase. With respect to the pronase treatment, however, all of the conditions except the pH of the pronase solution (7.2), employed with respect to the pepsin treatment of Example 1, were repeated in this Example.

The results shown in Table II again demonstrate that, in this case, with treatment of the dispersion, the membrane showed improved enzyme binding capacity. Furthermore, the length of the pronase treatment in this case appeared to have little effect on the results obtained, and as compared to fresh untreated dispersion, an increase in enzyme binding capacity of from 30 to over 57% was realized.

TABLE II

EFFECT OF PRONASE TREATMENT ON ENZYME BINDING CAPACITY OF COLLAGEN DISPERSION

| Pronase Treatment Time (Hr.) | | 0 | 1 | 3 | 6 | 9 | 12 | 24 |
|---|---|---|---|---|---|---|---|---|
| Telepiptide Removed Calculated from Tyresine Released (Based on Literature) | I | 0* | 40.0 | 46.7 | 54.7 | 62.4 | 62.4 | — |
| | II | 0* | — | 43.26 | 59.60 | — | 69.21 | 71.78 |
| Apparent Specific** Enzyme Activity (μmoles glucose/min/g-complex) | I | 493.69 | 607.32 | 627.15 | — | 704.41 | 770.21 | — |
| | II | 43.98 | — | 521.71 | 503.13 | — | 579.98 | 496.32 |
| Amount of Enzyme | I | — | — | — | — | — | — | — |

TABLE II-continued
EFFECT OF PRONASE TREATMENT ON ENZYME BINDING CAPACITY OF COLLAGEN DISPERSION

| Pronase Treatment Time (Hr.) |  | 0 | 1 | 3 | 6 | 9 | 12 | 24 |
|---|---|---|---|---|---|---|---|---|
| (mg enzyme/g-complex) | II*** | 61.0 | — | 93.5 | 96.0 | — | 94.5 | 90.0 |

*Neglegible amount of tyrosine found
**Average of two reactors
***Average of two determinations

EXAMPLE 3

A similar experiment was conducted using a fresh (un-aged) collagen film, prepared in the manner described in Example 1. Here however, the film was treated with pepsin for varying periods, and the results obtained are contained in Table III. The results in this case again show that a fresh-treated film can be produced which has an enhanced enzyme binding capacity. As shown in Table III, in this case about 23% increase in enzyme activity and amount of enzyme bound was realized.

EXAMPLE 4

In this Example, collagen films were again prepared in the manner described in Example 1. In this case, however, samples of the untreated membrane as well as samples of the membrane treated with the proteases pepsin, pronase and trypsin, each at various stages of natural aging, were each tested for enzyme binding capacity in the manner described above. The results obtained are shown in Table IV, and they again demonstrate the improved enzyme binding capacity, both with fresh and aged film, by treatment in accordance with the present invention.

EXAMPLE 5

In this example, a collagen film was prepared, again in the manner described in Example 1, but in this case the film was chemically, rather than naturally cross-linked. A 0.1% and 0.5% Glutaraldehyde treatment was employed in each case, and both the untreated and pepsin treated films were tested for specific activity.

TABLE III
EFFECT OF PEPSIN TREATMENT ON ENZYME BINDING CAPACITY OF FRESH COLLAGEN FIBERS

|  | Untreated Control | Treatment Time (Hrs.) | | | |
|---|---|---|---|---|---|
|  |  | 3 | 6 | 9 | 12 |
| c/o Telopeptide Removed Calculated from Tyrosine Released | — | 19.5 | 31.1 | 35.5 | 43.4 |
| Apparent specific enzyme activity*** (units/g-complex) | 490.78 | 588.69 | 572.79 | 598.45 | 609.32 |
| Amount of enzyme*** bound (mg lactase/g-complex) | 71 | 92 | 88 | 101 | 105 |

**Percentage based on literature
***Average of two determinations

TABLE IV
EFFECT OF TREATMENT WITH VARIOUS PROTEASES ON THE ENZYME BINDING CAPACITY OF AGED COLLAGEN MEMBRANE

|  | Age of collagen membrane (days) | Apparent specific enzyme activity (Units/g-complex) | Amount of bound enzyme (mg enzyme/g-complex) |
|---|---|---|---|
| Untreated Control | 0 | 568.16 | 139 |
|  | 21 | 474.34 | 87 |
|  | 42 | 422.94 | 66 |
| Pepsin Treated | 0 | 672.85 | 193 |
|  | 21 | 714.62 | 204 |
|  | 42 | 593.34 | 174 |
| Pronase Treated | 0 | 634.29 | 181 |
|  | 21 | 638.78 | 184 |
|  | 42 | 582.71 | 172 |
| Trypsin Treated | 0 | 541.84 | 123 |
|  | 21 | 481.22 | 94 |
|  | 42 | 430.32 | 76 |

The results obtained were as follows:

| Glutaraldehyde Treatment | Specific Activity (per moles/min/gm of complex) | | % Increase |
|---|---|---|---|
|  | No pepsin | Pepsin |  |
| 0.1%, for 5 min. | 104.1 | 136.2 | 32 |
| 0.5%, for 1 min. | 79.2 | 88.9 | 13 |

These results demonstrate the improved enzyme binding capacity of collagen films which have been chemically cross-linked.

What is claimed is:

1. A method for preparing an enzyme-membrane complex which comprises providing a membrane of collagen, said collagen including a well-ordered crystalline region and a telopeptide region, treating said membrane with a proteolytic enzyme selected from the group consisting of pepsin, trypsin, pronase, and mixtures thereof at a temperature between about 15° and 25° C., and for a period of from about 1 to 12 hours, swelling said membrane at a pH of between about 2 and 12, washing said swollen membrane, and complexing an enzyme to said washed membrane by contacting said membrane with an aqueous solution of an enzyme, said contacting of said membrane with said enzyme being carried out for a period of between about 12 and 48 hours and at a temperature of between about 4° and 15° C.

2. The method of claim 1 wherein said proteolytic enzyme comprises pepsin, and is maintained in an aqueous solution at a pH from 2 to 4 for from about 1 to 12 hours.

3. The method of claim 1 wherein said proteolytic enzyme comprises pronase, and is maintained in an aqueous solution at a pH of from 6 to 8 for from about 1 to 6 hours.

4. The method of claim 3 wherein said pH is maintained at about 7.2.

5. The method of claim 1 wherein said membrane is prepared by casting a film from a dispersion of said collagen.

6. The method of claim 5 wherein said film is aged for a period of from 3 to 200 days prior to said treatment with said proteolytic enzyme.

7. The method of claim 5 wherein said proteolytic enzyme comprises pepsin.

8. An enzyme-membrane complex containing greater than about 100 mg of said enzyme per gram of said complex prepared by the process of claim 1.

9. The enzyme-membrane complex of claim 8 wherein said enzyme complexed to said membrane is selected from the group consisting of lysozyme, urease, amylase, invertase, cellulase, glucose isomerase, $\beta$-galactosidase, and compatible mixtures thereof.

10. A method for preparing an enzyme-membrane complex which comprises preparing a dispersion of collagen, said collagen including a well-ordered crystalline region and a telopeptide region, treating said collagen in the dispersion with a proteolytic enzyme selected from the group consisting of pepsin, trypsin, pronase, and mixtures thereof at a temperature of between about 15° and 25° C. for a period of from about 1 to 12 hours, casting a membrane of said collagen, swelling said membrane at a pH of between about 2 and 12, washing said swollen membrane and complexing an enzyme to said washed membrane by contacting said membrane with an aqueous solution of an enzyme, said contacting of said membrane with said enzyme being carried out for a period of between about 12 and 48 hours and at a temperature of between about 4° and 15° C.

11. The method of claim 10 wherein said enzyme to be complexed with said membrane is selected from the group consisting of oxidoreductases, transferases, hydrolases, isomerases, and compatible mixtures thereof.

12. The method of claim 10 wherein said enzyme to be complexed with said membrane is selected from the group consisting of lysozyme, urease, amylase, invertase, cellulase, glucose-isomerase, B-galactosidase and compatible mixtures thereof.

13. The method of claim 10 including drying said enzyme-membrane complex.

14. An enzyme-membrane complex containing greater than about 100 mg of said enzyme per gram of said complex prepared by the process of claim 10.

* * * * *